United States Patent [19]

Cascone

[11] 4,123,262

[45] Oct. 31, 1978

[54] DENTAL GOLD ALLOY

[75] Inventor: Paul J. Cascone, New Rochelle, N.Y.

[73] Assignee: Pennwalt Corporation, Philadelphia, Pa.

[21] Appl. No.: 813,363

[22] Filed: Jul. 6, 1977

[51] Int. Cl.² .............................................. C22C 5/00
[52] U.S. Cl. .................................. 75/165; 75/134 B; 75/134 N; 75/134 T; 75/172 G; 32/8
[58] Field of Search ............... 75/172 G, 165, 134 N, 75/134 B, 134 T; 32/8

[56] References Cited

U.S. PATENT DOCUMENTS

| | | | |
|---|---|---|---|
| 1,987,451 | 1/1935 | Taylor | 75/165 |
| 2,143,217 | 1/1939 | Truthe | 75/135 |
| 3,134,671 | 5/1964 | Prosen | 75/172 |
| 3,374,123 | 3/1968 | Masumoto et al. | 148/11.5 |
| 3,495,972 | 2/1970 | Baum | 75/134 |
| 3,574,610 | 4/1971 | Prosen | 75/165 |
| 3,574,611 | 4/1971 | Prosen | 75/165 |
| 3,667,936 | 6/1972 | Katz | 75/134 N |
| 3,716,356 | 2/1973 | Burnett | 75/165 |
| 3,767,391 | 10/1973 | Tuccillo | 75/165 X |
| 3,819,366 | 6/1974 | Katz | 75/172 G X |
| 3,892,564 | 7/1975 | Hatswell | 75/165 |
| 3,981,723 | 9/1976 | Tuccillo | 75/165 |
| 4,062,676 | 12/1977 | Knosp | 75/165 |

OTHER PUBLICATIONS

Waterstrat et al., *Public Health Reports*, HEW vol. 79, No. 7, pp. 638–642, Jul. 1964.

*Primary Examiner*—M. J. Andrews
*Attorney, Agent, or Firm*—Edward A. Sager

[57] ABSTRACT

A silverless gold alloy consists of about 50–58% gold, 0.5–10.5% indium, 0.5–8.5% tin or 1.0–3.0% gallium, and the balance palladium. This alloy has physical properties similar to ADA Spec. No. 5 for Type IV dental casting gold alloys; and it may have porcelain fused thereto for making dental prosthetic appliances, with little chance that the porcelain will be stained.

10 Claims, No Drawings

DENTAL GOLD ALLOY

This invention relates to a silverless, gold base alloy to which porcelain may be fused when preparing dental prosthetic appliances. The alloy of the present invention has physical properties similar to the criteria for bridgework specified by the American Dental Association, i.e. Specification No. 5 for Type IV dental casting gold alloys; it also has a melting temperature below 2500° F.; and it has good ductility, i.e. its elongation in one inch is at least 10%.

The presence of silver in a dental gold alloy used for preparing baked-on ceramic to gold dental restorations has been known to cause staining of the porcelain at the juncture of the porcelain and the metal. A silverless gold alloy having no such propensity for staining porcelain is advantageous when preparing dental appliances intended to improve the appearance of the wearer as well as to restore function. The silverless, low gold content alloy disclosed herein has the desirable physical properties and non-staining feature, plus castability without difficulty at a temperature below 2500° F.

The alloy of the present invention is similar in many respects to the alloy disclosed in U.S. Pat. No. 3,981,723 and No. 3,961,420 (both assigned to the assignee of the present invention) except that it does not contain silver. The prior art alloy of U.S. Pat. No. 3,819,366 discloses an alloy to which porcelain may be fused, and which has a high percentage of precious metal alloy, but which discloses an alloy composition including zinc which has a high vapor pressure at the melting temperature of the alloy. Ingredients with high vapor pressure at the melting temperature of the alloy will adversely affect the castability of the alloy, and the alloy disclosed herein is superior in that regard also.

According to the present invention, the gold alloy consists approximately, in percentage by weight, of 50 to 58% gold, 0.5 to 10.5% indium; 0.5 to 8.5% tin or 1.0 to 3.0% gallium; and the balance palladium; wherein in the absence of gallium, the alloy contains at least 0.5% tin; wherein in the absence of tin the alloy contains at least 1% gallium; and, if tin is present, the total of indium and tin is preferably 10% in order to obtain optimum hardness.

The preferred composition of an alloy in accordance with the present invention is 51.5% gold; 8.5% indium; 1.5% gallium and 38.5% palladium.

Interestingly, it was found that Brinell Hardness increased almost linearly (except at both extremes) in proportion to tin content in an alloy containing 50 to 53% gold, various combinations of indium plus tin totalling 10%, and the balance palladium. In such an alloy, for example, Brinell Hardness ranged from about 158 with the tin content 2.5% to about 239 with 9% tin present, in nearly a linear relationship.

The following examples setting forth the physical properties of representative white gold alloys demonstrate the criticality of the present composition with regard to the attainment of the desired physical properties. All physical properties for said alloys have been measured after heat treating by heating in a furnace to 1900° F. at a rate of 75° to 100° F. per minute, holding at 1900° F. for about 10 minutes, and removing the specimen from the furnace and cooling under a refractory cover.

In the following tables for alloy Example Nos. 1 to 6, compositions given are in percents by weight, and elongation or ductility is percent elongation over one inch, and the term "ultimate tensile strength" is abbreviated as "Ult. Tensile Strength".

ALLOY EXAMPLE NO. 1

| Composition | Physical Properties | |
|---|---|---|
| Gold - 50.5% | Ult. Tensile Strength | 109,000 psi |
| Palladium - 39.5% | Yield Strength | 84,000 psi |
| Tin - 6% | Elongation | 13.5% |
| Indium - 4% | Brinell Hardness | 212 |

This is an example of an alloy having 50 to 53% gold, with various combinations of indium plus tin totalling 10%, and the balance palladium.

ALLOY EXAMPLE NO. 2

| Composition | Physical Properties | |
|---|---|---|
| Gold - 52% | Ult. Tensile Strength | 114,000 psi |
| Palladium - 39% | Yield Strength | 100,000 psi |
| Tin - 9% | Elongation | 5% |
| | Brinell Hardness | 230 |

The ductility of this alloy example is much too low without indium present. However, ductility may be improved if some indium is added in place of the tin, as in:

ALLOY EXAMPLE NO. 3

| Composition | Physical Properties | |
|---|---|---|
| Gold - 52% | Ult. Tensile Strength | 94,500 psi |
| Palladium - 39% | Yield Strength | 74,000 psi |
| Tin - 8.5 | Elongation | 13.5% |
| Indium - 0.5% | Brinell Hardness | 190 |

The added indium increased the alloy's ductility to a more favorable level. i.e. above 10%.

However, an alloy of all indium also produces a satisfactory material, as in:

ALLOY EXAMPLE NO. 4

| Composition | Physical Properties | |
|---|---|---|
| Gold - 51.7% | Ult. Tensile Strength | 99,000 psi |
| Palladium - 37.8% | Yield Strength | 71,500 psi |
| Indium - 10.5% | Elongation | 22% |
| | Brinell Hardness | 170 |

For the higher gold content alloys, the all indium alloy, however, is too soft since Brinell Hardness is less than 170, as in:

ALLOY EXAMPLE NO. 5

| Composition | Physical Properties | |
|---|---|---|
| Gold - 58% | Ult. Tensile Strength | 80,000 psi |
| Palladium - 33% | Yield Strength | 67,000 psi |
| Indium - 9% | Elongation | 10% |
| | Brinell Hardness | 158 |

Hardness and other physical properties are improved if a small amount of tin is added to this alloy, as in:

ALLOY EXAMPLE NO. 6

| Composition | Physical Properties | |
|---|---|---|
| Gold - 58% | Ult. Tensile Strength | 98,000 psi |

-continued

| Composition | Physical Properties | |
|---|---|---|
| Palladium - 32.5% | Yield Strength | 75,000 psi |
| Indium - 9% | Elongation | 12.4% |
| Tin - 0.5% | Brinell Hardness | 187 |

For the higher gold range, then, the addition of small quantities of tin can increase the physical properties above the criteria.

For the lower gold range of 50 to 53%, with indium and tin totalling 10% and the balance being palladium, however, alloys having higher than 6% indium fall below the physical property requirement for hardness, i.e. Brinell hardness is less than 170.

Alloy Example No. 4 above shows that the very high indium content alloy just barely exceeds the required physical properties. The addition of gallium instead of tin, however, increases the physical properties to a much higher level, as in the following examples: (Nos. 7 through 11)

In the tables below, the numbers in columns beside the listed elements are in percents by weight, "UTS (Ksi)" designates ultimate tensile strength in thousands of pounds per square inch, "YS" designates yield strength in the same units as UTS (Ksi), "Elong." designates ductility in percent elongation over one inch, and "BHN" refers to Brinell hardness number.

ALLOY EXAMPLE NOS. 7 TO 11

|  | 7 | 8 | 9 | 10 | 11 |
|---|---|---|---|---|---|
| Au | 53.5 | 52.25 | 51.5 | 50.75 | 50.5 |
| Pd | 35.0 | 37.0 | 38.5 | 40.0 | 40.0 |
| In | 8.0 | 9.5 | 8.5 | 7.5 | 6.5 |
| Ga | 1.5 | 1.25 | 1.5 | 1.85 | 3.0 |
| UTS (Ksi) | 110 | 109 | 120 | 102 | 108 |
| YS (Ksi) | 84 | 80 | 83 | 72 | 85 |
| Elong. | 10 | 16 | 22 | 24 | 15 |
| BHN | 214 | 195 | 200 | 185 | 195 |

Alloys outside of these ranges produce materials which are either too brittle as in Examples 12 and 14, or too soft as in Example No. 13:

ALLOY EXAMPLE NOS. 12 TO 14

|  | 12 | 13 | 14 |
|---|---|---|---|
| Au | 51.5 | 53 | 50 |
| Pd | 37.0 | 39 | 40 |
| In | 10.0 | 7 | 5 |
| Ga | 1.5 | 1 | 5 |
| UTS (Ksi) | 105 | 81 | 108 |
| YS (Ksi) | 89 | 43 | 108 |
| Elong. | 4.1 | 28 | 0 |
| BHN | 200 | 127 | 272 |
| Remarks | brittle | soft | brittle |

From the foregoing it can be seen that a silverless, white gold alloy for preparing dental prostheses may be provided which meets the physical properties criteria of ADA Spec. No. 5 for Type IV dental casting gold alloys, and which also has good ductility and castability, including a melting point below 2500° F. Such an alloy consists approximately, in percent by weight, of 50 to 58% gold; 0.5 to 10.5% indium; 0.5 to 8.5% tin or 1.0 to 3.0% gallium; and the balance palladium.

In the absence of gallium, such an alloy having a relatively high range of gold content, 53 to 58%, will also contain 6 to 10.5% indium, 0.5 to 4% tin, and the balance palladium. Also in the absence of gallium, such an alloy having a relatively low range of gold content, 50 to 53%, will also contain 4 to 6% indium, 4 to 6% tin, and the balance palladium. However, for optimum hardness of a relatively low gold content alloy having no gallium, the total of indium plus tin should be about 10%.

If gallium is present in the alloy instead of tin, the approximate composition range is 50 to 54% gold, 6.0 to 9.5% indium, 1 to 3% gallium, and the balance palladium. This is the preferred composition and more particularly the preferred embodiment thereof consists essentially of 51.5% gold, 8.5% indium, 1.5 gallium, and 38.5% palladium.

The invention disclosed herein may be practiced by providing an alloy with 50 to 58% gold, 0.5 to 10.5% indium, 0 to 8.5% tin, 0 to 3% gallium, and the balance palladium, to have the desired physical properties, including an elongation of at least 10% over one inch and a melting point less than 2500° F. However, in the absence of gallium, there should be at least 0.5% tin with a preferred total of indium plus tin of about 10%, and in the absence of tin there should be at least 1% gallium.

The invention contemplates the making of a dental appliance or restoration by casting the alloy disclosed herein, and preferably bonding porcelain to at least a portion of its surface.

Detailed instructions for making a baked-on ceramic to gold dental appliance or restoration are given in U.S. Pat. No. 3,981,723 following the examples. Such instructions are incorporated herein by reference to such patent.

What is claimed is:

1. A dental gold alloy consisting, in percent by weight, of about: 50 to 58% gold, 0.5 to 10.5% indium, 0.5 to 8.5% tin or 1.0 to 3.0% gallium, and the balance palladium; said alloy being non-staining and bondable to porcelain, castable without difficulty below 2500° F., and having at least 10% elongation in one inch.

2. An alloy in accordance with claim 1 containing approximately: 50 to 53% gold, 4 to 6% indium, 4 to 6% tin, and the balance palladium.

3. An alloy in accordance with claim 2 wherein the total of indium and tin is about 10%.

4. An alloy in accordance with claim 1 containing, approximately: 53 to 58% gold; 6 to 10.5% indium; 0.5 to 4% tin; and the balance palladium.

5. An alloy in accordance with claim 1 containing, approximately: 50 to 54% gold; 6 to 9.5% indium; 1 to 3% gallium; and the balance palladium.

6. An alloy in accordance with claim 5 consisting of 51.5% gold; 8.5% indium; 1.5% gallium; and 38.5% palladium.

7. A dental appliance comprised of the cast alloy of claim 1.

8. A dental appliance according to claim 7 having porcelain bonded to a surface portion thereof.

9. A dental gold alloy consisting, in percent by weight, of about: 50 to 58% gold, 0.5 to 10.5% indium, 0 to 8.5% tin, 0 to 3% gallium, and the balance palladium; when gallium is absent at least 0.5% tin is present, when tin is absent at least 1% gallium is present; and when gallium and tin are both absent about 10.5% indium is present; said alloy being non-staining and bondable to porcelain and having a liquidus temperature below 2500° F. and at least 10% elongation in one inch.

10. An alloy in accordance with claim 9 wherein the total of indium and tin is about 10%, and gallium is absent.

* * * * *

Dedication 4,123,262.—*Paul Joseph Cascone*, New Rochelle, N.Y. DENTAL GOLD ALLOY. Patent dated Oct. 31, 1978. Dedication filed July 10, 1980, by the assignee, *Pennwalt Corporation*.

Hereby dedicates to the Public all claims of said patent.

[*Official Gazette September 9, 1980.*]